United States Patent [19]

Schechter et al.

[11] Patent Number: 4,908,369
[45] Date of Patent: Mar. 13, 1990

[54] USE OF 1,4-DISUBSTITUTED-PIPERIDINYL COMPOUNDS IN THE MANUFACTURE OF A MEDICAMENT FOR THE TREATMENT OF INSOMNIA

[75] Inventors: Paul J. Schechter; John M. Orwin, both of Strasbourg, France; Christian K. Hinze, Rheinau-Honau, Fed. Rep. of Germany

[73] Assignee: Merrell Dow Pharmaceuticals Inc., Cincinnati, Ohio

[21] Appl. No.: 299,913

[22] Filed: Jan. 19, 1989

[30] Foreign Application Priority Data

Jan. 21, 1988 [EP] European Pat. Off. ........ 88400131.4

[51] Int. Cl.$^4$ ........................................... A61K 31/435
[52] U.S. Cl. ................................................. 514/277
[58] Field of Search ....................................... 514/277

[56] References Cited

PUBLICATIONS

Chem. Abst. 106-156281K (1987).
5-Hydroxytryptamine-2 antagonist increase human slow wave sleep, Brian Research, 378,(1986) 164–168 Idzikowski, et al.
Does ritanserin, a potent serotonin-S₂ antagonists, store energetic functions during the night? Journal of the Royal Society of Medicine, vol. 80, pp. 409–413, (1987), Janssen.
No Evidence of Sedative Effects From Ritanserin in Healthy Volunteers. Collegium Internationale Neuro-Psychopharmacologicum, San Juan, Puerto Rico/-Caribe Hilton International, Dec. 14–17, 1986.
Evidence for serotonin-S₂ receptor involvement in analgesia in humans, from the European Journal of Pharmacology, 130(1986) 311–314, Sandrini, et al.
Safety Evaluation of Ritanserin-An Investigational Serotonin Antagonist, from the Drug Intelligence and Clinical Pharmacy, vol. 20, Oct. 1986, Barone, et al.

Primary Examiner—Stanley J. Friedman
Attorney, Agent, or Firm—J. Michael Dixon

[57] ABSTRACT

The present invention pertains to the use of 1,4-disubstituted-piperidinyl compounds in the treatment of insomnia.

Said compounds have the following general formula:

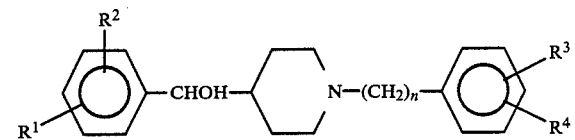

wherein:
each of $R^1$, $R^2$, $R^3$, and $R^4$ is independently selected from the group consisting of hydrogen, a $C_{1-6}$ alkyl group, halogen, trifluoromethyl, hydroxy, a $C_{1-6}$ alkoxy group, or an amino group; n is 2, 3, or 4; and the pharmaceutically acceptable acid addition salts thereof.

20 Claims, No Drawings

USE OF 1,4-DISUBSTITUTED-PIPERIDINYL COMPOUNDS IN THE MANUFACTURE OF A MEDICAMENT FOR THE TREATMENT OF INSOMNIA

The present invention pertains to the use of 1,4- disubstituted piperidinyl compounds in the manufacture of a medicament for the treatment of insomnia.

In accordance with the present invention it has been discovered that insomnia can be treated, that is relieved or alleviated, in a patient in need thereof by the administration of a hypnotic quantity of a compound of the formula :

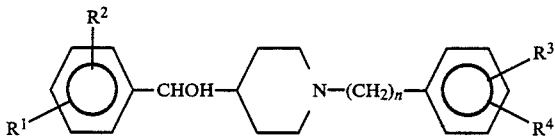

wherein:
each of $R^1$, $R^2$, $R^3$, and $R^4$ is independently selected from the group consisting of hydrogen, a $C_{1-6}$ alkyl group, halogen, trifluoromethyl, hydroxy, a $C_{1-6}$ alkoxy group, or an amino group; n is 2, 3, or 4; and the pharmaceutically acceptable acid addition salts thereof.

As used in this application:

(a) The term $C_{1-6}$ alkyl refers to a straight chain or branched alkyl group containing up to 6 carbon atoms. Representative examples of suitable alkyl groups include, methyl, ethyl, propyl, isopropyl, n-butyl, t-butyl, pentyl, hexyl, cyclopropyl, and cyclopentyl. Methyl and ethyl are currently preferred.

(b) The term halogen refers to a fluorine, bromine, chlorine or iodine atom. Fluorine and chlorine are currently preferred.

(c) The term $C_{1-6}$ alkOxy refers to a straight chain or branched alkoxy group containing up to 6 carbon atoms. Representative examples of suitable alkoxy groups include methoxy, ethoxy, propoxy, isopropoxy, butoxy, pentoxy, and hexyloxy.

(d) The term hydroxy in this application refers to the following substituent —OH.

(e) The term amino refers to —$NH_2$.

(f) The term "patient" as used herein is taken to mean warm-blooded animals, such as mammals, for example, dogs, rats, mice, cats, guinea pigs, horses, cattle, sheep and primates, including humans.

(g) The term insomnia as used in this application refers to a condition where a patient experiences symptoms such as, difficulty in falling asleep, frequent nocturnal awakenings, frequent early morning awakenings, etc.

(h) The term hypnotic as used in this application refers to the ability to induce sleep.

The expression "pharmaceutically acceptable acid addition salts" is intended to apply to any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic 2-phenoxybenzoic and sulfonic acids such as methane sulfonic acid and 2-hydroxyethane sulfonic acid.

Some of the compounds represented by Formula I exist as optical isomers. Any reference in this application to the compounds of Formula I, is meant to encompass a specific isomer or a mixture of isomers.

In those instances where $R^1$–$R^4$ are other than hydrogen, the substituents may be located at any position of the phenyl ring (i.e., meta, para, or ortho). Para is currently preferred for monosubstituted phenyl moieties. The 2,3-, 2,4- 2,5-, 3,4-, or 3,5-disubstituted phenyl moieties are also embraced herein.

$R^1$, $R^2$, $R^3$, and $R^4$ can each be the same or different substituents.

It is currently preferred for n to be either 2 or 3, with 2 being most preferred. It is also currently preferred for $R^3$ and $R^4$ to be hydrogen.

Representative examples of preferred compounds include:

(1) α-phenyl-1-(2-phenethyl)-4-piperidine methanol;
(2) α-phenyl-1-(3-phenpropyl)-4-piperidine methanol;
(3) α(4-methylphenyl)-1-(2-phenethyl)-4-piperidine methanol;
(4) α-(4-methoxyphenyl)-1-(2-phenethyl)-4-piperidine methanol;
(5) α-(3,5-dimethylphenyl)-1-(2-phenethyl)-4- 0 piperidine methanol;
(6) α-(3-(trifluoromethyl)phenyl)-1-(2-phenethyl)-4-piperidine methanol;
(7) α-(2,3-dimethoxyphenyl)-1-(2-phenethyl)-4piperidine methanol;
(8) α-(4-fluorophenyl)[1-(2-phenylethyl)-4-piperidinyl]-methanol;
(9) α-phenyl-[1-(4-phenylbutyl)-4-piperidinyl]-methanol;
(10) α-(3,4-dimethoxyphenyl-[1-(2-phenylethyl)-4-piperidinyl]-methanol;
(11) α-phenyl-[1-(4-aminophenylethyl)-4-piperidinyl]-methanol;
(12) α-phenyl-[1-(4-methoxyphenylethyl)-4-piperidinyl]-methanol;
(13) α-(4-methoxyphenyl)-[1-(4-methoxyphenylethyl)-4-piperidinyl]-methanol;
(14) α-(2,3-dimethoxyphenyl)-[1-(4-methoxyphenylethyl)]-methanol;
(15) α-phenyl-[1-(4-methoxyphenylethyl-4-piperidinyl]-methanol;
(16) α-phenyl-[1-(4-fluorophenylethyl)-4-piperidinyl]-methanol;
(17) α-(4-hydroxyphenyl)-[1-(2-phenylethyl)-4-piperidinyl]-methanol;
(18) α-(3,4-dihydroxyphenyl)-[1-(2-phenylethyl)-4-piperidinyl]-methanol, and
(19) α-(3,4-dichlorophenyl)-1-(2-phenylethyl)-4-piperidine methanol.

The compounds of Formula I, their methods of preparation and their use as serotonin $5HT_2$ antagonists are known in the art. European Patent Application No. 0 208 235 discloses these compounds and several methods for preparing these compounds. Any of these methods, or any other method known in the art, are suitable for preparing the compounds to be utilized in the method of the present invention.

The compounds encompassed by Formula I are hypnotic agents. They are useful in the treatment of insomnia. Patients suffering from insomnia, who are administered one of these compounds, will experience less difficulty in falling asleep, fewer nocturnal awakenings, etc.

The quantity of compound required to produce the hypnotic effect described above will vary with the particular compound utilized, the patient, the route of administration, the severity of the patient's insomnia, the presence of other underlying disease states in the patient, and other medications which are being administered concurrently to the patient. Generally though, a patients insomnia will respond to dosage range of from 0.1 to 10 mg/kg/day.

The compounds of Formula I can be administered either orally or parenterally. Repetitive daily administration may be desirable and will vary with the dosage form utilized, as well as the other parameters described above for the quantity of compound required.

The compounds of Formula I can be compounded into a variety of dosage forms, such as for example, tablets, capsules, solutions, elixirs, sterile solutions for injection and sustained release preparations. Methods for producing these dosage forms are well known in the art and are disclosed in European Patent Application 0 208 235.

What is claimed is:

1. A method for the treatment of insomnia comprising administering to a patient suffering from insomnia, a hypnotic quantity of a compound of the formula:

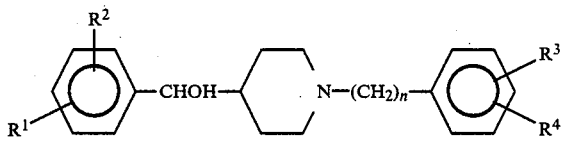

wherein n is 2, 3, or 4, each of $R^1$, $R^2$, and $R^4$ is independently selected from hydrogen, halogen, trifluoromethyl, $C_{1-6}$ alkyl, $C_{1-16}$ alkoxy, hydroxy or amino; or a pharmaceutically acceptable acid addition salt thereof.

2. A method according to claim 1 wherein said compound is α-phenyl-1-(2-phenethyl)-4-piperidine methanol.

3. A method according to claim 1 wherein said compound is α-phenyl-1-(3-phenpropyl)-4-piperidine methanol.

4. A method according to claim 1 wherein said compound is α-(4-methylphenyl)-1-(2-phenethyl)-4-piperidine methanol.

5. A method according to claim 1 wherein said compound is α-(4-methoxyphenyl)-1-(2-phenethyl)-4-piperidine methanol.

6. A method according to claim 1 wherein said compound is α-(3,5-dimethylphenyl)-1-(2-phenethyl)-4-piperidine methanol.

7. A method according to claim 1 wherein said compound is α-(3-(trifluoromethyl)phenyl)-1-(2-phenethyl)-4-piperidine methanol.

8. A method according to claim 1 wherein said compound is α-(2,3-dimethoxyphenyl)-1-(2-phenethyl)-4-piperidine methanol.

9. A method according to claim 1 wherein said compound is α-(4-fluorophenyl)[1-(2-phenylethyl)-4-piperidinyl]-methanol.

10. A method according to claim 1 wherein said compound is α-phenyl-[1-(4-phenylbutyl)-4-piperidinyl]-methanol.

11. A method according to claim 1 wherein said compound is α-(3,4-dimethoxyphenyl-[1-(2-phenylethyl)-4-piperidinyl]-methanol.

12. A method according to claim 1 wherein said compound is α-phenyl-[1-(4-aminophenylethyl)-4-piperidinyl]-methanol.

13. A method according to claim 1 wherein said compound is α-phenyl-[1-(4-methoxyphenylethyl)-4-piperidinyl]-methanol.

14. A method according to claim 1 wherein said compound is α-(4-methoxyphenyl)-[1-(4-methoxyphenylethyl)-4-piperidinyl]-methanol.

15. A method according to claim 1 wherein said compound is α-(2,3-dimethoxyphenyl)-[1-(4-methoxyphenyl-ethyl)]-4-piperidinyl]-methanol.

16. A method according to claim 1 wherein said compound is α-phenyl-[1-(4-methoxyphenylethyl-4-piperidinyl]-methanol.

17. A method according to claim 1 wherein said compound is α-phenyl-[1-(4-fluorophenylethyl)-4-piperidinyl]-methanol.

18. A method according to claim 1 wherein said compound is α-(4-hydroxyphenyl)-[1-(2-phenylethyl)-4-piperidinyl]-methanol.

19. A method according to claim 1 wherein said compound is α-(3,4-dihydroxyphenyl)-[1-(2-phenylethyl)-4-piperidinyl]-methanol, and 20. A method according to claim 1 wherein said compound is α-(3,4-dichlorophenyl)-1-(2-phenylethyl)-4-piperidine methanol.

* * * * *

UNITED STATES PATENT AND TRADEMARK OFFICE
CERTIFICATE OF

PATENT NO. : 4,908,369

DATED : March 13, 1990

INVENTOR(S) : Paul J. Schechter et al.

It is certified that error appears in the above-identified patent and that said Letters Patent is hereby corrected as shown below:

At column 1, line 39, the patent reads "alkOxy" and should read --alkoxy--.

At column 2, lines 30-31, the patent reads "-4- 0 piperidine" and should read -- -4-piperidine --.

At column 2, lines 48-49, the patent reads "(4-methoxyphenylethyl)]-methanol;" and should read -- (4-methoxyphenylethyl)]-4-piperidinyl]-methanol; --.

At column 3, line 42, the patent reads "$R^1$, $R^2$, and $R^4$ is" and should read --$R^1$, $R_2$, $R^3$, and $R^4$ is--.

At column 3, line 44, the patent reads "$C_{1-16}$alkoxy" and should read --$C_{1-6}$ alkoxy--.

Signed and Sealed this

Tenth Day of September, 1991

Attest:

HARRY F. MANBECK, JR.

Attesting Officer

Commissioner of Patents and Trademarks